United States Patent
Hata et al.

(10) Patent No.: US 6,333,188 B1
(45) Date of Patent: Dec. 25, 2001

(54) LACTIC ACID BACTERIA PREPARATION HAVING BIOPURIFICATION ACTIVITY

(75) Inventors: Tadayo Hata, Tondabayashi; Toshiyuki Maruoka, Toyonaka, both of (JP)

(73) Assignee: BHPH Company Limited, Nassau (BS)

( * ) Notice: Subject to any disclaimer, the term of this patent is extended or adjusted under 35 U.S.C. 154(b) by 0 days.

(21) Appl. No.: 09/631,388

(22) Filed: Aug. 3, 2000

(51) Int. Cl.⁷ .............................. C12N 1/12; C12N 1/00; A01N 63/00; A01N 65/00
(52) U.S. Cl. .................... 435/252.4; 435/252.9; 435/253.4; 435/853; 424/93.1; 424/93.43; 424/93.45
(58) Field of Search ................. 435/252.4, 853, 435/252.9, 253.4; 424/93.1, 93.43, 93.45

(56) References Cited

U.S. PATENT DOCUMENTS

| 4,314,995 | 2/1982 | Hata et al. . |
| 4,579,734 | 4/1986 | Hata et al. . |
| 4,871,539 | * 10/1989 | Hata et al. . |

FOREIGN PATENT DOCUMENTS

| 55-48386 | 4/1980 | (JP) . |
| 55-143916 | 11/1980 | (JP) . |
| 60-149527 | 8/1985 | (JP) . |
| 363280027A | * 11/1988 | (JP) . |

* cited by examiner

*Primary Examiner*—Christopher R. Tate
*Assistant Examiner*—Michele C. Flood
(74) *Attorney, Agent, or Firm*—Armstrong, Westerman, Hattori, McLeland & Naughton, LLP

(57) ABSTRACT

Although the inventors previously found that the novel species designated *Lactobacillus clearans* was highly effective for health purposes, they noted in particular that this species lacked sufficient intestinal purification action. Efforts to produce a species of higher potency and the like to remedy this drawback led to the unavoidable conclusion that the use of a bacterium by itself produced limited results. The concurrent use of another active substance was thus considered in seeking a lactic acid bacteria preparation capable of invigorating healthy individuals, and of renewing a sense of well being and restored health in semi-sick individuals or semi-healthy individuals.

The invention relates to a lactic acid bacteria preparation, comprising viable cells of *Lactobacillus clearans*, and either or both of viable and killed cells of *Enterococcus faecalis* capable of reducing one or more of at least triglycerides and cholesterol.

2 Claims, No Drawings

LACTIC ACID BACTERIA PREPARATION HAVING BIOPURIFICATION ACTIVITY

BACKGROUND OF THE INVENTION

1. Field of the Invention

The present invention relates to a lactic acid bacteria preparation that is extremely significant for the health of humans and animals, wherein the concurrent use of *Lactobacillus clearans*, which was first isolated by the inventors and belongs to the Lactobacillus genus yet has specific characteristics not found in conventionally known bacteria, and either or both of viable or killed cells of *Enterococcus faecalis* (Enterococcus), which are profoundly involved in lipid metabolism, allows the advantages of each to be more clearly and effectively brought out.

2. Description of the Related Art

There are reportedly 300 species and 100 trillion individual bacteria in the intestines, weighing a total of 1 kg and far outnumbering the total of 60 trillion human cells. Years of immunological study and research have gradually elucidated their significant involvement in the health and various diseases of humans and animals, and experts now regard intestinal flora as a vital organ function. Beneficial bacteria belonging to the group of lactic acid bacteria, such as the Bifidobacterium genus and the Lactobacillus genus, co-exist in a balanced manner when predominant. This balance can be broken down by a variety of factors, such as changes in the amount and quality of daily diet, overexertion, sleeplessness, and mental stress, resulting in the proliferation of harmful bacteria such as Welch bacillus and Veillonella. The expulsion of beneficial bacteria results in greater production of harmful substances, which can lead to a variety of illnesses and accelerated aging overall, from feces disorders such as diarrhea and constipation, to those resulting from poisoned blood, such as chronic fatigue, chapped skin, hepatic dysfunction, hypertension and arteriosclerosis.

The Russian Metchnikoff (1845 to 1916) theorized that the primary cause of aging was poisoning from toxins formed by intestinal putrefying fermentation, and advocated as a remedy the habit of drinking lactic acid bacteria beverages such as yogurt to help prevent aging. Throughout the vagaries of the history of lactic acid bacteria since then, it has not been possible to grasp the true practical utility of such bacteria. That is because matters now revealed by immunological studies and elucidated by experiments could not be unraveled.

Metchnikoff's hypothesis has been borne out and is now common knowledge in the health sciences, as recent progress in microbiology has elucidated a variety of important functions by beneficial intestinal bacteria, such as the reduction in intestinal acidity and the promotion of intestinal motility to help in the digestion of foods and the absorption of nutrients, the simultaneous suppression and degradation of harmful substances, the synthesis of vitamins and amino acids, protection against intestinal infections by pathogens, and enhanced immunological power.

In addition, along with recent health trends, lactic acid bacteria have established a firm footing as beverages and antiflatulents for many people. It cannot be denied, however, that such products do not appeal to people who are looking for positive results, having failed to realize better health and improved symptoms through daily ingestion or use of lactic acid bacteria. Unfortunately, lactic acid bacteria products are still consumed merely as refreshment, or still tend to be regarded as a preference similar to coffee.

In view of the foregoing, there has been a need for a product which could be rapidly administered to bring out better effects unavailable in conventional lactic acid bacterial beverages or preparations. Although the inventors previously found that the novel species designated *Lactobacillus clearans* was highly effective for health purposes, they noted in particular that this species lacked sufficient intestinal purification action. Efforts to produce a strain of higher potency and the like to remedy this drawback led to the unavoidable conclusion that the use of the bacterium by itself produced limited results. The concurrent use of another active substance was thus considered in seeking a lactic acid bacteria preparation capable of invigorating healthy individuals, and of renewing a sense of well being and restored health in semi-sick individuals or semi-healthy individuals.

SUMMARY OF THE INVENTION

As a result of extensive research to find a compatible biological or non-biological partner to remedy the aforementioned drawbacks, the inventors perfected the present invention upon finding, among *Enterococcus faecalis* belonging to the same group of lactobacilli as *Lactobacillus clearans*, a species capable of reducing at least one among triglycerides and cholesterol. That is, the present invention is a lactic acid bacteria preparation, comprising viable cells of *Lactobacillus clearans*, and viable cells of *Enterococcus faecalis* capable of reducing one or more of at least triglycerides and cholesterol.

The second of the inventions is a lactic acid bacteria preparation, comprising viable cells of *Lactobacillus clearans*, and killed cells of *Enterococcus faecalis* capable of reducing one or more of at least triglycerides and cholesterol.

The third of the inventions is a lactic acid bacteria preparation, comprising viable cells of *Lactobacillus clearans*, and viable and killed cells of *Enterococcus faecalis* capable of reducing one or more of at least triglycerides and cholesterol.

DESCRIPTION OF THE PREFERRED EMBODIMENTS

The *Lactobacillus clearans* referred to in the present invention is a novel strain belonging to the Lactobacillus genus, and has the following biochemical characteristics 1, 2, 3, and 4. Specifically, it comprises strains of the Lactobacillus genus that 1) are capable of reducing both $Na_2S.9H_2O$ and $NH_4OH$ when 0.5 g $Na_2S.9H_2O$ and/or 0.5 mL $NH_4OH$ is or are added to 5 g meat extract, 5 g peptone, 1 g glucose, 1 g $CaCO_3$, and 1 L water (neutral pH); 2) show no growth-promoting action despite the addition of 0.5 g $Na_2S.9H_2O$ and/or 0.5 mL $NH_4OH$ during the logarithmic growth phase of bacterial culture in medium comprising 1 g casamino acid and vitamins (A: 900 IU; $B_1$: 1 mg; $B_2$: 1 mg; $B_6$: 1 mg; $B_{12}$: 5 γ; nicotinamide: 16 mg; calcium pantothenate: 8 mg; C: 64 mg; and $D_2$: 120 IU) in Stephenson-Wetham medium ((abbreviated as S-W) 1 g $KH_2PO_4$, 0.7 g $MgSO_4.7H_2O$, 1 g NaCl, 4 g $(NH_4)_2HPO_4$, 0.03 $FeSO_4.7H_2O$, and 5 g glucose); 3) have resistance, in the form of naturally isolated strains, to $Na_2S.9H_2O$ greater than that of conventionally known lactic acid bacteria but weaker than that of *Lactobacillus deodorans*; and 4) are gram positive, rod-shaped, non-motile, and catalase negative, are not nitrate-reducing and not gelatin-degrading, do not produce indole or hydrogen sulfide, have a high capacity for forming lactic acid from glucose and lactose, and have growth promoted by the addition of acetic acid (see Japanese Patent Publication(Kokoku) H4-632.

Advantages of *Lactobacillus clearans*, in addition to the action of common Lactobacillus, include potent intestinal purification action absent in conventional Lactobacillus as described in Japanese Patent 1714413 and Japanese Patent Application 11-15177, such as: 1) decomposition of intestinal putrefying malodorous substances; 2) increases in beneficial bacteria such as Bifidobacterium and Lactobacillus among the intestinal flora, with dramatic reductions in harmful bacteria such as Welch bacillus and Veillonella, thereby providing a better balance in the intestinal flora to improve the intestinal environment; and 3) suppression of the growth primarily of etiologic agents causing intestinal infections, and diminished toxicity.

This action will be described below through tests. In vitro tests were conducted first. 15 mL of a 10-fold dilution of feces was introduced into test tubes (18×180 mm). The test tubes were then inoculated with sample bacteria 1) that had been sterilized at high pressure for 15 minutes at 120° C. and 2) that had not been sterilized. The test tubes were stoppered with rubber plugs for 72 hours of anaerobic culture at 37° C. 1 mL air was then drawn by syringe from inside the test tubes and injected into 5 L odor bags for olfactory tests by a panel of 6 individuals. The odor was assessed based on the feces odor criteria given in Table 1.

TABLE 1

Feces odor criteria

| Odor ranks | Odor |
|---|---|
| 1 | faint odor recognizable as that of feces |
| 2 | easily recognizable as slight odor of feces |
| 3 | clearly recognizable as weak odor of feces |
| 4 | strong odor equal to untreated feces |
| 5 | extremely strong odor more pronounced than untreated feces |

Three typical strains of *Lactobacillus clearans*, specifically, FERM BP-6972, FERM BP-6971, FERM BP-6973, were used to test the deodorizing capacity in the aforementioned in vitro tests. The results in Table 2 show that the samples sterilized at high pressure were clearly deodorized, with an odor assessed as being the weak or slight odor of feces. The unsterilized samples, on the other hand, showed less deodorization than the samples sterilized at high pressure, because malodorous substances were produced, perhaps as a result of the activity of numerous putrefying bacteria in the feces, but they too were nevertheless clearly deodorized. The results for the 3 typical strains of *Lactobacillus clearans* in the aforementioned test were similarly reproduced with other similar strains.

TABLE 2

Deodorizing capacity of *Lactobacillus clearans* (in vitro)

| Inoculum strain | Odor (average value by panel) | |
|---|---|---|
| FERM BP-No. | High pressure sterilization | Unsterilized |
| 6972 | 2.5 | 2.8 |
| 6971 | 2.3 | 2.5 |
| 6973 | 2.0 | 2.3 |
| Not inoculated | 4.0 | 4.5 |

In subsequent in vivo tests, 150 mL yogurt prepared using *Lactobacillus clearans* FERM BP-6973 was ingested once a day, and the odor of feces was determined 20 to 30 days, 50 to 60 days, and 80 to 90 days after ingestion, with the averages given in Table 3. The results were determined by introducing 0.5 g feces samples from the 10 individuals into 20 L odor bags, which were stored at room temperature for evaluation of the odor by a panel of 6 individuals after 30 minutes. The average feces odor for 5 individuals ingesting no yogurt was rated as 100. Although feces odor varied considerably depending on the dietary contents, the average odor for 10 individuals ingesting yogurt decreased about 50% 1 month after ingestion, 70% after 2 months, and 85% after 3 months. After 3 months, however, continuous ingestion resulted in a peak odor reduction of 80 to 90%.

TABLE 3

Feces odor after ingestion of yogurt prepared using *Lactobacillus clearans*

| Odor when no yogurt ingested | Odor after ingestion of yogurt | | |
|---|---|---|---|
| | 20 to 30 days | 50 to 60 days | 80 to 90 days |
| 100 | 50 | 30 | 15 |

In terms of the correlation between purification and bacteria in the natural world, the inventors narrowed the analyzed substances into easily testable malodorous substances, which were broadly classified into sulfur compounds, nitrogen compounds, and carbon compounds. It was found that bacteria capable of degrading malodorous sulfur compounds such as $Na_2S.9H_2O$, malodorous nitrogen compounds such as $NH_3$, and malodorous carbon compounds such as acetic acid, butyric acid, and similar lower fatty acids were capable of degrading most malodorous sulfur, nitrogen, and carbon compounds of polymers therefrom, this being referred to as the SNC theory. The following tests were conducted in accordance with this theory.

0.5 g $Na_2S.9H_2O$ or 0.5 mL ammonia water ($NH_4OH$) was added to 1 mL synthetic medium comprising 5 g meat extract, 5 g peptone, 3 g sodium butyrate, 5 g glucose, and 3 g $CaCO_3$, the medium was inoculated with *Lactobacillus clearans* for 72 hours of anaerobic culture at 37° C., and the decrease in the $Na_2S.9H_2O$ or $NH_4OH$ that had been added was determined over time. The $Na_2S.9H_2O$ was measured by the iodine titration method of JIS K0102-1985, and the $NH_4OH$ was measured by the indole phenol blue absorbance method of JIS K0102-1985. The results are given in Tables 4 and 5. The tables show that *Lactobacillus clearans* had the capacity to reduce toxic malodorous $Na_2S.9H_2O$ and $NH_4OH$ 40 to 50% in 72 hours. This means that it can degrade and assimilate most other malodorous toxic substances.

TABLE 4

Degradation and assimilation of sodium disulfide by *Lactobacillus clearans*

| Inoculum strain FERM BP-No. | Concentration when added | $Na_2S.9H_2O$ concentration and percent decrease | | |
|---|---|---|---|---|
| | | 24 hours | 48 hours | 72 hours |
| 6972 | 500 ppm | 400 ppm 20% decrease | 350 ppm 30% decrease | 300 ppm 40% decrease |

TABLE 4-continued

Degradation and assimilation of sodium disulfide by *Lactobacillus clearans*

| Inoculum strain FERM BP- No. | Concentration when added | $Na_2S.9H_2O$ concentration and percent decrease | | |
|---|---|---|---|---|
| | | 24 hours | 48 hours | 72 hours |
| 6971 | 500 ppm | 380 ppm 24% decrease | 330 ppm 34% decrease | 275 ppm 45% decrease |
| 6973 | 500 ppm | 350 ppm 30% decrease | 300 ppm 40% decrease | 250 ppm 50% decrease |

TABLE 5

Degradation and assimilation of ammonia by *Lactobacillus clearans*

| Inoculum strain FERM BP- No. | Concentration when added | $NH_4OH$ concentration and percent decrease | | |
|---|---|---|---|---|
| | | 24 hours | 48 hours | 72 hours |
| 6972 | 500 ppm | 400 ppm 20% decrease | 350 ppm 30% decrease | 300 ppm 40% decrease |
| 6971 | 500 ppm | 375 ppm 25% decrease | 300 ppm 40% decrease | 280 ppm 44% decrease |
| 6973 | 500 ppm | 375 ppm 25% decrease | 300 ppm 40% decrease | 250 ppm 50% decrease |

The above in vitro sensory tests and chemical analysis were described as methods for assessing the deodorizing action of *Lactobacillus clearans*. The 10-fold dilutions of feces samples prepared at this time were centrifuged before culture and 72 hours after culture, 5 mL supernatant was collected and diluted 10-fold to determine the $S^{2+}$ and $NH_4^+$ ion concentrations, and the extent of their decrease was calculated. The results in Table 6 show that the decrease in the $S^{2+}$ and $NH_4^+$ ions in feces were even higher than the decrease in the aforementioned synthetic medium, indicating that feces was a more suitable habitat for *Lactobacillus clearans*. The $S^{2+}$ ions were determined by the iodine titration method of JIS K0102-1985, and the $NH_4^+$ ions were determined by the indole phenol blue absorbance method of JIS K0102-1985.

TABLE 6

Decrease in $S^{2+}$ and $NH_4^+$ by *Lactobacillus clearans*

| 10-fold feces dilution | Inoculum FERM BP- No. | $S^{2+}$ concentration and decrease | | $NH_4^+$ concentration and decrease | |
|---|---|---|---|---|---|
| | | Before culture | 72 hours culture | Before culture | 72 hours culture |
| Sterilized at high pressure | 6972 | 30 ppm | 15 ppm 50% decrease | 350 ppm | 190 ppm 45% decrease |
| | 6971 | 30 ppm | 12 ppm 60% decrease | 350 ppm | 130 ppm 63% decrease |
| | 6973 | 30 ppm | 10 ppm 67% decrease | 350 ppm | 110 ppm 68% decrease |
| Not sterilized | 6972 | 52 ppm | 35 ppm 33% decrease | 385 ppm | 235 ppm 40% decrease |
| | 6971 | 52 ppm | 30 ppm 42% decrease | 385 ppm | 200 ppm 48% decrease |
| | 6973 | 52 ppm | 25 ppm 52% decrease | 385 ppm | 165 ppm 57% decrease |

2 µL of the aforementioned supernatant was introduced into a gas chromatograph to analyze the lower fatty acids. The gas chromatography involved the use of Col. unisole F-200 30/60 glass (3 §×3 m) at a carrier gas rate of 50 mL/min (He), with 152 kPa (0.55 kg/cm²G) hydrogen and 152 kPa (0.55 kg/cm²G) air, at a column temperature of 140° C. and Inj 200° C. The assayed substances were acetic acid, propionic acid, iso-butyric acid, n-butyric acid, iso-valeric acid, and n-valeric acid, with the calculated concentrations given in Table 7. Table 7 shows that the concentrations of lower fatty acids decreased 50 to 75% with samples sterilized at high pressure, and 40 to 60% with unsterilized samples.

TABLE 7

Decrease in lower fatty acids by *Lactobacillus clearans*

| 10-fold feces dilution | Inoculum FERM BP-No. | Total lower fatty acid concentration and decrease | |
|---|---|---|---|
| | | Before culture | 72 hours culture |
| Sterilized at high pressure | 6972 | 2850 ppm | 1500 ppm 47% decrease |
| | 6971 | 2850 ppm | 960 ppm 66% decrease |
| | 6973 | 2850 ppm | 750 ppm 74% decrease |
| Not sterilized | 6972 | 3500 ppm | 2100 ppm 40% decrease |
| | 6971 | 3500 ppm | 1800 ppm 48% decrease |
| | 6973 | 3500 ppm | 1280 ppm 63% decrease |

Lyophilized cells of three typical strains of *Lactobacillus clearans*, that is, FERM BP-6972, 6971, and 6973, were prepared, and were mixed in equal parts to form a preparation. 2 g of the preparation (5×10⁸ cells/g) was taken continuously, and the changes in the cell count (cells/1 g feces) of Bifidobacterium and Lactobacillus (except for *Lactobacillus clearans*) which are known as typical beneficial bacteria in the intestinal flora, as well as of typical harmful bacteria such as Veillonella and *Clostridium perfringens* (Welch bacillus), were measured over time. Table 8 shows the results of oral administration to 20 healthy individuals, and Table 9 shows the results of oral administration to 20 constitutionally weak individuals.

TABLE 8

Effects of oral administration of *actobacillus clearans* preparation on intestinal flora of healthy individuals mean values for 20 healthy individuals)

| | | Cell count before administration | Cell count after administration | | | | |
|---|---|---|---|---|---|---|---|
| | | | 1 month | 2 months | 3 months | 6 months | 12 months |
| Beneficial bacteria | Bifidobacterium | $1.2 \times 10^{10}$ | $1.5 \times 10^{10}$ | $1.8 \times 10^{10}$ | $2.1 \times 10^{10}$ | $2.4 \times 10^{10}$ | $2.8 \times 10^{10}$ |
| | Lactobacillus | $2 \times 10^{7}$ | $2.5 \times 10^{7}$ | $3 \times 10^{7}$ | $5 \times 10^{7}$ | $1 \times 10^{8}$ | $2 \times 10^{8}$ |
| Harmful bacteria | Clostridium | $1 \times 10^{5}$ | $8 \times 10^{4}$ | $7 \times 10^{4}$ | $5 \times 10^{4}$ | $2 \times 10^{4}$ | $1 \times 10^{4}$ |
| | Veillonella | $5 \times 10^{5}$ | $4.5 \times 10^{5}$ | $4 \times 10^{5}$ | $3 \times 10^{5}$ | $2 \times 10^{5}$ | $1 \times 10^{5}$ |

TABLE 9

Effects of oral administration of *Lactobacillus clearans* preparation on intestinal flora of constitutionally weak individuals (mean values for 20 constitutionally weak individuals)

| | | Cell count before administration | Cell count after administration | | | | |
|---|---|---|---|---|---|---|---|
| | | | 1 month | 2 months | 3 months | 6 months | 12 months |
| Beneficial bacteria | Bifidobacterium | $5 \times 10^{9}$ | $5 \times 10^{9}$ | $6 \times 10^{9}$ | $6.5 \times 10^{9}$ | $7.5 \times 10^{9}$ | $1 \times 10^{10}$ |
| | Lactobacillus | $1 \times 10^{7}$ | $1.2 \times 10^{7}$ | $1.5 \times 10^{7}$ | $2.5 \times 10^{7}$ | $3 \times 10^{7}$ | $7 \times 10^{7}$ |
| Harmful bacteria | Clostridium | $5 \times 10^{5}$ | $3.5 \times 10^{5}$ | $3 \times 10^{5}$ | $2.5 \times 10^{5}$ | $2 \times 10^{5}$ | $1 \times 10^{5}$ |
| | Veillonella | $2 \times 10^{6}$ | $1.7 \times 10^{6}$ | $1.4 \times 10^{6}$ | $1.1 \times 10^{6}$ | $5 \times 10^{5}$ | $3 \times 10^{5}$ |

Tables 8 and 9 show that before the administration of the *Lactobacillus clearans* preparations, the beneficial bacteria among the intestinal flora were an average of 220% greater in healthy individuals than in constitutionally weak individuals, whereas harmful bacteria were only about 22.5%. This shows that the state of the intestinal flora is an index of the current state of health, that is, how deeply involved the intestinal flora are in health. A new finding was that ingestion of the preparation first resulted in an increase in beneficial bacterial in healthy individuals, and that with this increase, there was a gradual decrease in harmful bacteria. In contrast to this pattern, the pattern found in constitutionally weak individuals was that the harmful bacteria first decreased, followed by a gradual increase in beneficial bacteria. Overall, the average changes in beneficial and harmful bacteria reflected an increase in beneficial bacteria and a corresponding decrease in harmful bacteria. This trend accelerated after 3 months, with Bifidobacterium increasing 50% after 6 months and 110% after 1 year, and with Lactobacillus increasing 300% after 6 months and 950% after 1 year. In contrast, the Clostridium decreased 70% after 6 months and 85% after 1 year, while the Veillonella decreased 67.5% after 6 months and 82.5% after 1 year.

*Escherichia coli* O-157, *Salmonella enteitidis*, and *Shigella flexneri* were cultured alone and together with *Lactobacillus clearans* (FERM BP-6973) to check the action of *Lactobacillus clearans* against pathogens, and the results were compared. The medium composition used for the cultures comprised 10 g meat extract, 10 g peptone, 2 g glucose, 2 g NaCl, and 1 g $CaCO_3$ per liter, with the pH adjusted to 7.2. Anaerobic culture was performed at 37° C., with subcultures repeated every 72 hours, at which point the plates were diluted and smeared to monitor the changes in cell count, whether the colonies were the S type (original) or had mutated into the R type with diminished toxicity, their ratio, and the like. The pathogens used in the tests were acquired from Medic KK (registered sanitation research institute).

Table 10 shows the results of *E. coli* O-157 cultured by itself, and Table 11 shows the results of mixed culture of *E. coli* O-157 and *Lactobacillus clearans*. Table 10 shows that in cultures of *E. coli* O-157 alone, the cell count was a virtually constant 4 to $5 \times 10^9$ cells/g throughout 20 subcultures, with no R types showing up. Table 11 shows that in mixed cultures of *E. coli* O-157 and *Lactobacillus clearans*, there was little change in the *Lactobacillus clearans* cell count, but that there were significant changes in the cell count of the *E. coli* O-157. R types showed up at the $5^{th}$ subculture, and the ratio of R types increased with the accumulation of subsequent subcultures, until all cells formed R types by the $18^{th}$ subculture. There was no reversion to the S type in subsequently continued subcultures.

TABLE 10

Results of cultures of *E. coli* O-157 by itself

| | *E. coli* O-157 | | |
|---|---|---|---|
| Number of subcultures | Number of S type cells | Number of R type cells | Ratio of R type cells |
| 1 | $5 \times 10^{9}$ | 0 | 0% |
| 3 | $4.5 \times 10^{9}$ | 0 | 0% |
| 5 | $4.7 \times 10^{9}$ | 0 | 0% |
| 7 | $4.4 \times 10^{9}$ | 0 | 0% |
| 10 | $4.3 \times 10^{9}$ | 0 | 0% |
| 12 | $4.5 \times 10^{9}$ | 0 | 0% |
| 15 | $4 \times 10^{9}$ | 0 | 0% |
| 18 | $3.8 \times 10^{9}$ | 0 | 0% |
| 20 | $4.2 \times 10^{9}$ | 0 | 0% |

TABLE 11

Results of cultures of mixed cultures of *E. coli*
O-157 and *Lactobacillus clearans*

| Number of subcultures | Cell count of FERM BP-6973 | *E. coli* O-157 Number of S type cells | Number of R type cells | Number of R type cells |
|---|---|---|---|---|
| 1 | $1.2 \times 10^9$ | $5 \times 10^9$ | 0 | 0% |
| 3 | $1.2 \times 10^9$ | $3.5 \times 10^9$ | 0 | 0% |
| 5 | $1.4 \times 10^9$ | 0 | $1.9 \times 10^9$ | 100% |
| 7 | $1 \times 10^9$ | $1 \times 10^9$ | $1 \times 10^9$ | 50% |
| 10 | $7 \times 10^8$ | $1.2 \times 10^9$ | $2.2 \times 10^9$ | 65% |
| 12 | $1.1 \times 10^9$ | $5 \times 10^8$ | $2 \times 10^9$ | 80% |
| 15 | $1.2 \times 10^9$ | $2 \times 10^8$ | $3.2 \times 10^9$ | 94% |
| 18 | $1.5 \times 10^9$ | 0 | $1.7 \times 10^9$ | 100% |
| 20 | $1.3 \times 10^9$ | 0 | $1.2 \times 10^9$ | 100% |

Table 12 shows the results obtained with *Salmonella enteritidis* cultured by itself, and Table 13 shows the results obtained with mixed cultures of *Salmonella enteritidis* and *Lactobacillus clearans*. Table 12 shows that in cultures of *Salmonella enteritidis* alone, the cell count was 3 to $5 \times 10^9$ cells/g. R types showed up sponeously in the $14^{th}$ subculture, reaching a ratio of 5% by the $20^{th}$ subculture. The ratio increased in subsequent subcultures, peaking at 23% by the $50^{th}$ subculture. The ratio of R types thereafter stayed at about 20%. Table 13 shows that in mixed cultures of *Salmonella enteritidis* and *Lactobacillus clearans*, the ratio of R types was 29% in the $5^{th}$ subculture, and that the ratio of R types increased with the accumulation of subsequent subcultures, reaching 50% in the $10^{th}$ subculture, 90% in the $20^{th}$ subculture, and 100% in the $47^{th}$ subculture. S type reversion in subsequent subcultures was less than 1%. After the $70^{th}$ subculture, all S types disappeared, with no further reversion.

TABLE 12

Results of cultures of *Salmonella enteritidis* by itself

| Number of subcultures | *Salmonella enteritidis* Number of S type cells | Number of R type cells | Ratio of R type cells |
|---|---|---|---|
| 1 | $5 \times 10^9$ | 0 | 0% |
| 5 | $4 \times 10^9$ | 0 | 0% |
| 10 | $3 \times 10^9$ | 0 | 0% |
| 15 | $3 \times 10^9$ | $1 \times 10^8$ | 3% |
| 20 | $3 \times 10^9$ | $1.5 \times 10^8$ | 5% |
| 25 | $3.5 \times 10^9$ | $2 \times 10^8$ | 5% |
| 30 | $4 \times 10^9$ | $5 \times 10^7$ | 1% |
| 35 | $3.7 \times 10^9$ | $3 \times 10^8$ | 8% |
| 40 | $3.2 \times 10^9$ | $5 \times 10^8$ | 14% |
| 47 | $3 \times 10^9$ | $7 \times 10^8$ | 19% |
| 50 | $3.3 \times 10^9$ | $1 \times 10^9$ | 23% |
| 55 | $2.8 \times 10^9$ | $8 \times 10^8$ | 22% |
| 60 | $3 \times 10^9$ | $7 \times 10^8$ | 17% |
| 65 | $3.2 \times 10^9$ | $5 \times 10^8$ | 14% |
| 70 | $2.8 \times 10^9$ | $6 \times 10^8$ | 18% |
| 75 | $3 \times 10^9$ | $7 \times 10^8$ | 19% |
| 80 | $2.7 \times 10^9$ | $5 \times 10^8$ | 16% |

TABLE 13

Results of mixed cultures of *Salmonella enteritidis* and *Lactobacillus clearans*

| Number of Subcultures | Cell count of FERM BP-6973 | *Salmonella enteritidis* Number of S type cells | Number of R type cells | Ratio of R type cells |
|---|---|---|---|---|
| 1 | $1 \times 10^9$ | $5 \times 10^9$ | 0 | 0% |
| 5 | $5 \times 10^8$ | $2.5 \times 10^9$ | $1 \times 10^9$ | 29% |
| 10 | $3 \times 10^8$ | $1 \times 10^9$ | $1 \times 10^9$ | 50% |
| 15 | $4 \times 10^8$ | $5 \times 10^8$ | $1.5 \times 10^9$ | 75% |
| 20 | $3 \times 10^8$ | $2 \times 10^8$ | $2 \times 10^9$ | 90% |
| 25 | $3.5 \times 10^8$ | $1.5 \times 10^8$ | $2 \times 10^9$ | 93% |
| 30 | $3 \times 10^8$ | $1.6 \times 10^7$ | $8 \times 10^9$ | 98% |
| 35 | $2 \times 10^8$ | $1.5 \times 10^8$ | $1 \times 10^9$ | 87% |
| 40 | $2.5 \times 10^8$ | $1 \times 10^8$ | $1.5 \times 10^9$ | 94% |
| 47 | $3 \times 10^8$ | 0 | $2 \times 10^9$ | 100% |
| 50 | $5 \times 10^8$ | $3 \times 10^7$ | $2 \times 10^9$ | 99% |
| 55 | $6 \times 10^8$ | 0 | $2.1 \times 10^9$ | 100% |
| 60 | $5 \times 10^8$ | $1 \times 10^7$ | $1.8 \times 10^9$ | 99% |
| 65 | $7.5 \times 10^8$ | $2 \times 10^7$ | $2 \times 10^9$ | 99% |
| 70 | $8 \times 10^8$ | 0 | $2.2 \times 10^9$ | 100% |
| 75 | $7 \times 10^8$ | 0 | $2 \times 10^9$ | 100% |
| 80 | $7.5 \times 10^8$ | 0 | $1.8 \times 10^9$ | 100% |

Table 14 shows the results of *Shigella flexneri* cultured by itself, and Table 15 shows the results of mixed culture of *Shigella flexneri* and *Lactobacillus clearans*. Table 14 shows that in cultures of *Shigella flexneri* alone, R types showed up spontaneously in the $10^{th}$ subculture, reaching a ratio of 9% by the $20^{th}$ subculture. The ratio increased in subsequent subcultures, peaking at 20% by the $40^{th}$ subculture. The ratio of R types thereafter stayed at about 10 to 20%. Table 15 shows that in mixed cultures of *Shigella flexneri* and *Lactobacillus clearans*, R types showed up in the $5^{th}$ subculture, and that the ratio of R types increased with the accumulation of subsequent subcultures, reaching 100% in the $80^{th}$ subculture. There was S type reversion in subsequent subcultures, but less than 1%. After the $108^{th}$ subculture, all S types disappeared, with no further reversion.

TABLE 14

Results of cultures of *Shigella flexneri* by itself

| Number of Subcultures | *Shigella flexneri* Number of S type cells | Number of R type cells | Ratio of R type cells |
|---|---|---|---|
| 1 | $5 \times 10^9$ | 0 | 0% |
| 5 | $5 \times 10^9$ | 0 | 0% |
| 10 | $4 \times 10^9$ | $5 \times 10^7$ | 1% |
| 15 | $4 \times 10^9$ | $1 \times 10^8$ | 2% |
| 20 | $4.2 \times 10^9$ | $4 \times 10^8$ | 9% |
| 25 | $3.8 \times 10^9$ | $5 \times 10^8$ | 12% |
| 30 | $3.7 \times 10^9$ | $6 \times 10^8$ | 14% |
| 35 | $3.8 \times 10^9$ | $5 \times 10^8$ | 12% |
| 40 | $4 \times 10^9$ | $1 \times 10^9$ | 20% |
| 45 | $4 \times 10^9$ | $7 \times 10^8$ | 15% |
| 50 | $4.2 \times 10^9$ | $7 \times 10^8$ | 14% |
| 55 | $4 \times 10^9$ | $1 \times 10^8$ | 20% |
| 75 | $3.6 \times 10^9$ | $8 \times 10^8$ | 18% |
| 80 | $3.5 \times 10^9$ | $7 \times 10^8$ | 17% |
| 90 | $3.5 \times 10^9$ | $6 \times 10^8$ | 15% |
| 100 | $3.2 \times 10^9$ | $6 \times 10^8$ | 16% |
| 110 | $3.7 \times 10^9$ | $7 \times 10^8$ | 16% |

TABLE 15

Results of mixed cultures of *Shigella flexneri* and *Lactobacillus clearans*

| Number of Subcultures | Cell count of FERM BP-6973 | *Shigella flexneri* Number of S type cells | Number of R type cells | Ratio of R type cells |
|---|---|---|---|---|
| 1 | $1.2 \times 10^9$ | $5 \times 10^9$ | 0 | 0% |
| 5 | $8 \times 10^8$ | $3 \times 10^9$ | $2 \times 10^8$ | 6% |
| 10 | $5 \times 10^8$ | $2.5 \times 10^9$ | $1 \times 10^9$ | 29% |
| 15 | $3 \times 10^8$ | $2.5 \times 10^9$ | $1.5 \times 10^9$ | 38% |
| 20 | $3 \times 10^8$ | $2 \times 10^9$ | $2 \times 10^9$ | 50% |
| 25 | $3 \times 10^8$ | $1.8 \times 10^9$ | $2 \times 10^9$ | 53% |
| 30 | $3.5 \times 10^8$ | $1.8 \times 10^9$ | $2.2 \times 10^9$ | 55% |
| 35 | $3 \times 10^8$ | $1 \times 10^9$ | $2.5 \times 10^9$ | 71% |
| 40 | $2.8 \times 10^8$ | $8 \times 10^8$ | $3 \times 10^9$ | 79% |
| 45 | $2.6 \times 10^8$ | $5 \times 10^8$ | $3 \times 10^9$ | 85% |
| 50 | $3 \times 10^8$ | $1 \times 10^9$ | $2.8 \times 10^9$ | 74% |
| 55 | $3.2 \times 10^8$ | $5 \times 10^8$ | $3 \times 10^9$ | 85% |
| 75 | $3.5 \times 10^8$ | $3 \times 10^7$ | $3.3 \times 10^9$ | 99% |
| 80 | $3.2 \times 10^8$ | 0 | $3.2 \times 10^9$ | 100% |
| 90 | $3 \times 10^8$ | $5 \times 10^7$ | $3 \times 10^9$ | 99% |
| 100 | $3 \times 10^8$ | $3 \times 10^7$ | $3 \times 10^9$ | 99% |
| 110 | $3.2 \times 10^8$ | 0 | $3 \times 10^9$ | 100% |

Goups of ten 8-week old male mice were intraperitoneally administered $1 \times 10^8$ cells per animal to study the toxicity of the S and R types of *E. coli* O-157, *Salmonella enteritidis*, and *Shigella flexneri*. Conserved strains were used for the S types, and strains which had been mutated into 100% R types by *Lactobacillus clearans* were used at that point in time for the R types. The results in Table 16 show that all animals died within 4 days with S type pathogens, whereas none died with the R types except for *Shigella flexneri* which resulted in death by the $7^{th}$ day.

TABLE 16

Toxicity of S and R types of *E. coli* O-157, *Salmonella enteritidis*, and *Shigella flexneri* on mice

| | S type | R type |
|---|---|---|
| *E. coli* O-157 | Death after $3^{rd}$ day following administration (Course) immobilized on $2^{nd}$ day, followed by death | Survived administration (Course) virtually no movement for 2 days, matted fur, poor complexion $3^{rd}$ to $5^{th}$ day: occasionally ate and drank $5^{th}$ to $7^{th}$ day: increasingly active movement After $7^{th}$ day: normal activity |
| *Salmonella enteritidis* | Death after $4^{th}$ day following administration (same course as above) | Survived administration (same course as O-157) |
| *Shigella flexneri* | Death after $3^{rd}$ day following administration (same course as above) | $7^{th}$ day: Death (Course) virtual stasis starting on $2^{nd}$ day, but occasional drinking $5^{th}$ day on: indisposition and subsequent death |

The yogurt prepared with *Lactobacillus clearans* described above was orally administered to humans, and blood was analyzed once a month to study the changes in intestinal flora. Cholesterol and triglyceride levels fell about 10% in more than 80% of individuals compared to before administration.

Table 17 shows the differences in function between the *Lactobacillus clearans* of the present invention and conventional *Lactobacillus* strains.

TABLE 17

Comparison of functions between *Lactobacillus clearans* and conventional *Lactobacillus* strains

| Parameter | *Lactobacillus clearans* | Conventional *Lactobacillus* strains |
|---|---|---|
| Action against toxic, maladorous intestinal putrefying substances such as sulfur, nitrogen, and carbon compounds | degrades, breaks down, and denatures most toxic malodorous compounds such as sulfur, nitrogen, and carbon compounds to reduce them | degrades and reduces malodorous carbon compounds, but not toxic malodorous compounds such as sulfur and nitrogen compounds |
| Feces deodorization | ++ | – to ± |
| Action on beneficial intestinal bacteria | considerable increases | increases with continued ingestion in some people |
| Bifidobacterium | 2 to 10-fold | 1 to 3-fold |
| Lactobacillus | 10 to 100-fold | less than 10-fold |
| Action on harmful intestinal bacteria | harmful bacterial strongly suppressed with considerable increases | suppressing action, but not with most |
| Veillonella | $\frac{1}{20}$ to $\frac{1}{100}$ | 1 to $\frac{1}{5}$ |
| Clostridium | $\frac{1}{20}$ to $\frac{1}{100}$ | 1 to $\frac{1}{5}$ |
| Antiflatulent action | ++ | – to + |
| Nutrient requirements | low to moderate | high |
| Intestinal proliferation | + | – to + |
| Intestinal stationary ability | – to + | – |
| Action on coexisting pathogens | mutated into non-pathogens (S to R mutation) | no effect coexistence with any pathogens |
| Salmonella | pathogenicity lost by $47^{th}$ subculture | succumbs in competition with pathogens during subculture |
| *Shigella flexneri* | pathogenicity lost by $108^{th}$ subculture | |
| *E. coli* (O-157) | pathogenicity lost by $18^{th}$ subculture | |
| Cholesterol and triglycerides | weak, but able to reduce | none |

*Enterococcus faecalis* is a group of bacteria constituting the intestinal flora and belongs to the group of lactic acid bacteria, normally occurring in an amount of about $1 \times 10^7$ cells per gram feces. They appear in the form of two spherical or ovoid shapes, or in the form of short chains. They are gram positive cocci with potent resistance to heat, drying, chlorine, gallic acid, and the like, and grow in a wider temperature range of 10 to 45° C. compared to common streptococci. Although there are some pathogenic strains, they are nontoxic. The viable cells act as antiflatulents, and have been commercially available for more than 10 years in Japan. They have been proven to be nontoxic when taken orally. Apart from such commercial products, viable and killed cells of some strains have recently been shown to effectively lower blood cholesterol and triglycerides. They thus hold promise in the prevention or treatment of typically related adult diseases (diseases stemming from life style habits), such as hyperlipidemia, hypertension, and arteriosclerosis. The *Enterococcus faecalis* referred to in the present invention indicates strains having such functions.

The following is an example of a method for preparing viable cells of *Enterococcus faecalis* for use in the present invention. Specifically, cells which have been cultured and centrifuged by a common method are suspended in physiological saline, washed, centrifuged again, and collected. They may be lyophilized using soluble starch as a preservative. As an example of a method for preparing killed cells of *Enterococcus faecalis*, soluble starch and the washed and centrifuged cells obtained when the aforementioned viable cells have been collected can be treated for 30 minutes in 100° C. hot water and then lyophilized.

Although *Enterococcus faecalis* has no in vitro capacity for reducing sodium sulfide ($Na_2S.9H_2O$) or ammonia, it does have a weak deodorizing capacity against 10-fold dilution of feces. Table 18 gives the deodorizing capacity of two typical strains of *Enterococcus faecalis*, namely, FERM BP-7230 and FERM BP-7231. The test was the same as that for *Lactobacillus clearans*, and the criteria were the same as those given in Table 1.

TABLE 18

Deodorizing capacity of *Enterococcus faecalis* (in vitro)

|  |  | Odor (average value by panel) | |
| --- | --- | --- | --- |
| Inoculum FERM BP-No. |  | High pressure sterilization | Unsterilized |
| 7230 | Viable cells | 3.0 | 3.5 |
|  | Killed cells | 4.0 | 4.0 |
| 7231 | Viable cells | 3.2 | 3.5 |
|  | Killed cells | 4.0 | 4.5 |

The two typical strains of Enterococcus faecalis were orally administered in amounts of $1 \times 10^9$ cells/person per day. Feces odor prior to administration was rated as 100. Feces odor was determined 20 to 30 days, 50 to 60 days, and 80 to 90 days following ingestion, with the results given in Table 19. Table 19 shows that odor was reduced by *Enterococcus faecalis*, albeit weakly.

TABLE 19 feces odor during ingestion of *Enterococcus faecalis*

| Inoculum FERM BP-No. |  | Odor prior to ingestion | Odor after ingestion | | |
| --- | --- | --- | --- | --- | --- |
|  |  |  | 20 to 30 days | 50 to 60 days | 80 to 90 days |
| 7230 | Viable cells | 100 | 90 | 80 | 65 |
|  | Killed cells | 100 | 90 | 83 | 77 |
| 7231 | Viable cells | 100 | 85 | 75 | 70 |
|  | Killed cells | 100 | 90 | 80 | 75 |

Viable and killed cells of two typical strains of *Enterococcus faecalis*, namely, FERM BP-7230 and BP-7231, were prepared and mixed in equal parts viable and killed cells to produce a preparation. The preparation was taken in an amount of $1 \times 10^9$ cells/day/person for 6 months, and the changes in the cell count of the intestinal flora were determined over time by measuring the changes in the cell count (cells/1 g feces)of Bifidobacterium and Lactobacillus (except for *Lactobacillus clearans*) which are known as typical beneficial bacteria, as well as of typical harmful bacteria such as Veillonella and *Clostridium perfringens*. Table 20 shows the results of oral administration to 10 healthy individuals. Table 20 shows that the viable cells had a slightly higher rate of improvement than the killed cells. The results were far lower than those of *Lactobacillus clearans*, however.

TABLE 20

Effect of oral administration of *Enterococcus faecalis* preparation on intestinal flora in healthy individuals

| | | Administration of viable cells | | | Administration of Killed cells | | |
| --- | --- | --- | --- | --- | --- | --- | --- |
| | | Cell count before admin. | Cell count after 6 months | | Cell count before admin. | Cell count after 6 months | |
| Beneficial bacteria | Bifidobacterium | $1.2 \times 10^{10}$ | $1.5 \times 10^{10}$ | 25% increase | $1.5 \times 10^{10}$ | $1.8 \times 10^{10}$ | 20% increase |
|  | Lactobacillus | $1.8 \times 10^7$ | $3 \times 10^7$ | 67% increase | $2 \times 10^7$ | $3 \times 10^7$ | 50% increase |
| Harmful bacteria | Clostridium | $1 \times 10^5$ | $0.7 \times 10^5$ | 30% decrease | $1.2 \times 10^5$ | $0.9 \times 10^5$ | 25% decrease |
|  | Veillonella | $5.5 \times 10^5$ | $4.4 \times 10^5$ | 20% decrease | $6 \times 10^5$ | $5 \times 10^5$ | 17% decrease |

Mixed cultures of *Escherichia coli* O-157, *Salmonella enteritidis*, and *Shigella flexneri* were performed to study the action of *Enterococcus faecalis* against pathogens. The ratios in which the pathogens mutated from S to R types were virtually the same as spontaneously occurring ratios. Pathogen cell counts gradually decreased with each subculture, until *Salmonella enteritidis* had disappeared by the 25th subculture, *Shigella flexneri* had disappeared by the 33rd subculture, and *E. coli* O-157 had disappeared by the 35th culture. Although this suggested that the growth of *Enterococcus faecalis* overcame pathogens, the potential production of some physiologically active substances suppressing pathogen growth could not be ruled out.

The aforementioned viable and killed cell preparations of *Enterococcus faecalis* were added, in amounts of $1\times10^9$ cells/1 gram feed each, to feed. Mice raised for 3 months on this and mice raised on conventional feed alone were compared for serum triglycerides and cholesterol. The mice were divided into groups of 10, and were allowed to feed freely. The triglycerides and cholesterol were measured by means of an E-Test Wako and C-Test Wako, respectively. The mean level for the control mice was 100%. The results are given in Table 21. Table 21 shows that mice continually ingesting either viable or killed cells had a 20 to 40% reduction in levels for both parameters, leaving no room for doubt as to their effectiveness.

TABLE 21

Effect of oral administration of *Enterococcus faecalis* preparation on serum triglyceride and cholesterol levels in mice

| Inoculum | Triglycerides | | Cholesterol | |
|---|---|---|---|---|
| FERM BP-No. | Viable cells | Killed cells | Viable cells | Killed cells |
| 7230 | 72% | 80% | 65% | 70% |
| 7231 | 68% | 65% | 60% | 57% |

Fifteen 8-week old spontaneous hypertensive rats (SHR) were divided into 3 groups. The groups were fed feed containing viable and killed cell preparations of *Enterococcus faecalis* in amounts of $1\times10^9$ cells/gram feed. The control group was not administered any cell preparation. The animals were raised for 3 months. Table 22 gives the blood pressure after 3 months. Table 22 shows an approximately 10% decrease in blood pressure.

TABLE 22:

effects of oral administration of *Enterococcus faecalis* preparation on rat blood pressure

| Inoculum | Blood pressure before admin. | Blood pressure after administration | | |
|---|---|---|---|---|
| FERM BP-No. | | Viable cells | Killed cells | Percent decrease |
| 7230 | 205 mmHg | 185 mmHg | 178 mmHg | 9.7 to 13% |
| 7231 | 208 mmHg | 190 mmHg | 185 mmHg | 7.3 to 9.7% |
| Control | 202 mmHg | | 210 mmHg | |

EXAMPLES

The combined action of *Lactobacillus clearans* and *Enterococcus faecalis* allowed surprisingly effective results to be rapidly obtained. Manufacturing methods and examples of the preparations in the present invention are described below, but the scope of the present invention is not limited by these manufacturing examples and working examples.

Manufacturing Example 1

Production of *Lactobacillus clearans* preparation: 10 L medium comprising 5 g meat extract, 5 g peptone, 3 g sodium acetate, 1 mL ammonia water, 10 g glucose, 0.5 g cystine, and 2 g yeast extract per liter medium was inoculated with *Lactobacillus clearans* for 72 hours of anaerobic culture at 37° C. The resulting culture was centrifuged, giving 10 g biomass. This was washed with 500 mL physiological saline and centrifuged, twice. The washed biomass was introduced into 500 mL solution comprising 50 g skim milk, 30 g trehalose, and 0.5 g taurine, and was thoroughly stirred. The mixture was lyophilized by a common method, giving 82.5 g cell preparation ($3\times10^9$ cell/g). This was mixed with 330 g thoroughly dried skim milk, giving a *Lactobacillus clearans* preparation containing $5\times10^8$ viable cells per gram.

Manufacturing Example 2

Production of *Enterococcus faecalis* viable cell preparation: 10 L medium comprising 5 g meat extract, 5 g peptone, 2 g sodium chloride, 2 g yeast extract, and 10 g glucose per liter medium was inoculated with *Enterococcus faecalis* for 72 hours of aerobic culture at 37° C. The resulting culture was centrifuged, giving 16 g biomass. This was washed with 800 mL physiological saline and centrifuged, twice. The washed biomass was introduced into 500 mL solution comprising 20 g skim milk, 30 g soluble starch, and 0.5 g sodium glutamate, and was thoroughly stirred. The mixture was lyophilized by a common method, giving 54 g cell preparation ($5\times10^9$ cell/g). This was mixed with 486 g thoroughly dried soluble starch, giving a *Enterococcus faecalis* viable cell preparation containing $5\times10^8$ viable cells per gram.

Manufacturing Example 3

Production of *Enterococcus faecalis* killed cell preparation: The washed biomass obtained in Manufacturing Example 2 was suspended in 500 mL physiological saline, 50 g soluble starch was then introduced, the solution was thermally sterilized for 15 minutes at 110° C., and the suspension was lyophilized by a common method, giving 53 g cell preparation (approximately $5\times10^9$ cells/g). Killed cell preparations can also be produced by rupturing the cells ultrasonically or the like.

Manufacturing Example 4

Production of *Lactobacillus clearans* and *Enterococcus faecalls* mixture preparation: The *Lactobacillus clearans* preparation produced in Manufacturing Example 1 and the *Enterococcus faecalis* viable cell preparation produced in Manufacturing Example 2 or the *Enterococcus faecalis* killed cell preparation produced in Manufacturing Example 3 were mixed in equal parts to produce a mixture preparation. The preparation in this case contained *Lactobacillus clearans* in an amount of $2.5\times10^8$ cells/g and *Enterococcus faecalis* in an amount of $2.5\times10^8$ cells/g, but the ratio between the *Lactobacillus clearans* and *Enterococcus faecalis* preparations can be varied during the manufacturing process to produce mixtures containing any desired cell count. The preparation may be in the form of powders, granules, capsules, or other common formulations with a suitable excipient.

Example 1

15 mL of a 10-fold dilution of feces was introduced into test tubes (18×180 mm). The test tubes were then inoculated with sample bacteria 1) that had been sterilized at high pressure for 15 minutes at 120° C. and 2) that had not been sterilized. The test tubes were stoppered with rubber plugs for 72 hours of anaerobic culture at 37° C. 1 mL air was then drawn by syringe from inside the test tubes and injected into 5 L odor bags for olfactory tests by a panel of 6 individuals. The odor was assessed based on the feces odor criteria given in Table 1. For *Enterococcus faecalis* killed cell preparations, 0.1 g of the preparation produced in Manufacturing Example 3 was added to the test tubes. The test results in Table 23 show that the feces odor was considerably weakened, particularly in the case of feces diluent treated with samples sterilized at high pressure. This will be evident in a comparison with the results for test batches inoculated with *Lactobacillus clearans* alone in Table 2.

TABLE 23 test of deodorization with mixture of
*Lactobacillus clearans* and *Enterococcus faecalis* (1)

| Cells used | | In vitro test | |
|---|---|---|---|
| *Lactobacillus clearans* FERM BP-No. | *Enterococcus faecalis* FERM BP-No. | Sterilized at high pressure | Unsterilized |
| 6973 | 7230 (viable) | 1.2 | 1.5 |
|  | 7230 (killed) | 1.3 | 1.7 |

Example 2

A combination of 1 g *Enterococcus faecalis* (FERM BP-7230) viable cell preparation or 1 g *Enterococcus faecalis* (FERM BP-7230) killed cell preparation and 100 mL yogurt prepared with *Lactobacillus clearans* FERM BP-6973 in medium comprising 100 g skim milk, 50 g sucrose, and 2 g agar per liter was continuously administered to 10 individuals, and the feces odor was continuously determined 20 to 30 days, 50 to 60 days, and 80 to 90 days after administration. The results were determined by introducing 0.5 g feces samples from the 10 individuals into 20 L odor bags, which were stored at room temperature for evaluation of the odor by a panel of 6 individuals after 30 minutes. The average feces odor for 5 individuals ingesting no yogurt was rated as 100. The mean values in Table 24 show that oral administration increasingly weakened feces odor over time. After 90 days, the odor was considerably diminished and was no longer disagreeable. The appreciable effects will be evident when compared with the results obtained with the administration of *Lactobacillus clearans* alone in Table 3.

TABLE 24 test of deodorization with mixture of
*Lactobacillus clearans* and *Enterococcus faecalis* (2)

| Cells used | | In vitro test | | |
|---|---|---|---|---|
| *Lactobacillus clearans* FERM BP-No. | *Enterococcus faecalis* FERM BP-No. | 20 to 30 days | 50 to 60 days | 80 to 90 days |
| 6973 | 7230 (viable) | 20 | 10 | 5 |
|  | 7230 (killed) | 33 | 16 | 8 |

Example 3

In the same manner as in Example 1, test tubes of 10-fold feces diluent were inoculated with sample bacteria 1) that had been sterilized at high pressure for 15 minutes at 120° C. and 2) that had not been sterilized. The test tubes were stoppered with rubber plugs for 72 hours of anaerobic culture at 37° C. The cultures were then centrifuged, 5 mL supernatant was collected from each and diluted 10-fold, and the concentrations of free sulfur ions ($S^{2+}$) and ammonium ions ($NH_4^+$) were determined in the resulting 50 mL solution. The concentration of lower fatty acids was also determined by gas chromatography. Tables 25 and 26 give the measured results. The tables show that typical substances in feces were reduced at a high rate of 70 to 90% by both sterilized and unsterilized samples. The rate of reduction will be evident in a comparison with the results obtained upon inoculation with *Lactobacillus clearans* alone in Tables 6 and 7.

TABLE 25

Test on decrease in toxic malodorous substances by mixture of *Lactobacillus clearans* and *Enterococcus faecalis* (1)
(sterilized feces dilution)

| Bacteria | | Results of study of chemical analysis | | | | | |
|---|---|---|---|---|---|---|---|
| *Lactobacillus clearans* | *Enterococcus faecalis* | Before culture (ppm) | | | After culture (ppm) | | |
| FERM BP-No. | FERM BP-No. | $S^{2+}$ | $NH_4^+$ | Fatty acids | $S^{2+}$ | $NH_4^+$ | Fatty acids |
| 6973 | 7230 (viable) | 30 | 350 | 2800 | 3 90% decrease | 70 80% decrease | 500 82% decrease |
|  | 7230 (killed) | 30 | 350 | 2800 | 4 87% decrease | 80 77% decrease | 620 78% decrease |

TABLE 26

Test on decrease in toxic malodorous substances by mixture of *Lactobacillus clearans* and *Enterococcus faecalis* (2)
(unsterilized feces dilution)

| Bacteria | | | | | Results of study of chemical analysis | | |
|---|---|---|---|---|---|---|---|
| *Lactobacillus clearans* | *Enterococcus faecalis* | | | | Before culture (ppm) | After culture (ppm) | |
| FERM BP-No. | FERM BP-No. | $S^{2+}$ | $NH_4^+$ | Fatty acids | $S^{2+}$ | $NH_4^+$ | Fatty acids |
| 6973 | 7230 (viable) | 50 | 370 | 3500 | 9 / 82% decrease | 65 / 82% decrease | 870 / 75% decrease |
|  | 7230 (killed) | 50 | 370 | 3500 | 12 / 76% decrease | 80 / 78% decrease | 1020 / 76% decrease |

Example 4

1 g *Lactobacillus clearans* preparation ($5 \times 10^8$ cells/g) comprising a mixture of equal parts of three typical strains of *Lactobacillus clearans*, specifically, FERM BP-6972, FERM BP-6971, FERM BP-6973, and 1 g *Enterococcus faecalis* viable cell preparation ($5 \times 10^8$ cells/g) of *Enterococcus faecalis* FERM BP-7230 or 1 g *Enterococcus faecalis* killed cell preparation ($5 \times 10^8$ cells/g) of *Enterococcus faecalis* FERM BP-7231 were continuously administered for 6 months to 20 healthy individuals and 20 constitutionally weak individuals. The intestinal flora were monitored over time, with the results given in Tables 27 and 28. The tables show that the oral administration of *Enterococcus faecalis* viable or killed cells mixed with *Lactobacillus clearans* more rapidly increased beneficial bacterial and decreased harmful bacteria than when *Lactobacillus clearans* was administered alone, as shown in Tables 8 and 9. That is, improvements were about 25% faster in healthy individuals, with a 10 to 50% higher beneficial bacterial cell count and a 20 to 40% lower harmful bacterial cell count. In constitutionally weak individuals, improvements were about 30% faster, with a 10 to 30% higher beneficial bacterial cell count and a 20 to 50% lower harmful bacterial cell count. It may thus be concluded that improvement in the intestinal flora was more effective in constitutionally weak individuals.

TABLE 27 effects of mixture of *Lactobacillus clearans* and *Enterococcus faecalis* on intestinal flora (healthy individuals)

| *Lactobacillus clearans* | *Enterococcus faecalis* | | Cell count before admin. | Change in cell count after administration | | | |
|---|---|---|---|---|---|---|---|
| | | | | 1 month | 2 months | 3 months | 6 months |
| FERM BP-6972 6971 6973 | FERM BP-7230 (viable cells) | Bifidobacterium | $1.25 \times 10^{10}$ | $1.65 \times 10^{10}$ | $2.0 \times 10^{10}$ | $2.3 \times 10^{10}$ | $2.8 \times 10^{10}$ |
| | | Lactobacillus | $2.4 \times 10^7$ | $4.0 \times 10^7$ | $6.5 \times 10^7$ | $10 \times 10^7$ | $15 \times 10^7$ |
| | | Clostridium | $1.2 \times 10^5$ | $0.8 \times 10^5$ | $0.5 \times 10^5$ | $0.3 \times 10^5$ | $0.1 \times 10^5$ |
| | | Veillonella | $5.0 \times 10^5$ | $4.0 \times 10^5$ | $2.5 \times 10^5$ | $2.0 \times 10^5$ | $1.0 \times 10^5$ |
| | FERM BP-7231 (killed cells) | Bifidobacterium | $1.25 \times 10^{10}$ | $1.60 \times 10^{10}$ | $1.0 \times 10^{10}$ | $2.20 \times 10^{10}$ | $2.65 \times 10^{10}$ |
| | | Lactobacillus | $2.4 \times 10^7$ | $3.5 \times 10^7$ | $5.8 \times 10^7$ | $8.5 \times 10^7$ | $14 \times 10^7$ |
| | | Clostridium | $1.2 \times 10^5$ | $1.0 \times 10^5$ | $0.7 \times 10^5$ | $0.4 \times 10^5$ | $0.13 \times 10^5$ |
| | | Veillonella | $5.0 \times 10^5$ | $4.0 \times 10^5$ | $3.0 \times 10^5$ | $2.3 \times 10^5$ | $1.2 \times 10^5$ |

TABLE 28 effects of mixture of *Lactobacillus clearans* and *Enterococcus faecalis* on intestinal flora (constitutionally weak individuals)

| *Lactobacillus clearans* | *Enterococcus faecalis* | | Cell count before admin. | Change inn cell count after administration | | | |
|---|---|---|---|---|---|---|---|
| | | | | 1 month | 2 months | 3 months | 6 months |
| FERM BP-6972 6971 6973 | FERM BP-7230 (viable cells) | Bifidobacterium | $4.5 \times 10^9$ | $5.5 \times 10^9$ | $7.0 \times 10^9$ | $8.0 \times 10^9$ | $10.0 \times 10^9$ |
| | | Lactobacillus | $1.0 \times 10^7$ | $1.2 \times 10^7$ | $1.8 \times 10^7$ | $3.0 \times 10^7$ | $5.0 \times 10^7$ |
| | | Clostridium | $4.5 \times 10^5$ | $2.5 \times 10^5$ | $1.8 \times 10^5$ | $1.4 \times 10^5$ | $1.0 \times 10^5$ |
| | | Veillonella | $2.2 \times 10^6$ | $1.6 \times 10^6$ | $1.0 \times 10^6$ | $0.65 \times 10^6$ | $0.38 \times 10^6$ |
| | FERM BP-7231 (killed cells) | Bifidobacterium | $4.5 \times 10^9$ | $5.0 \times 10^9$ | $6.0 \times 10^9$ | $7.0 \times 10^9$ | $9.0 \times 10^9$ |
| | | Lactobacillus | $1.0 \times 10^7$ | $1.1 \times 10^7$ | $1.5 \times 10^7$ | $2.3 \times 10^7$ | $4.5 \times 10^7$ |
| | | Clostridium | $4.5 \times 10^5$ | $2.8 \times 10^5$ | $2.0 \times 10^5$ | $1.5 \times 10^5$ | $1.0 \times 10^5$ |
| | | Veillonella | $2.20 \times 10^6$ | $1.70 \times 10^6$ | $1.20 \times 10^6$ | $0.75 \times 10^6$ | $0.4 \times 10^6$ |

Example 5

Viable or killed cells of *Enterococcus faecalis* were added to mixed cultures of *Lactobacillus clearans, E.coli* O-157, *Salmonella enteritidis*, or *Shigella flexneri* for anaerobic culture at 37° C., and subcultures were repeated every 72 hours, at which point the plates were diluted and smeared to monitor the changes in cell count and the ratio of S-R mutation of *E. coli* O-157, *Salmonella enteritidis*, and *Shigella flexneri*. The results are given in Tables 29, 30, 31, 32, 33, and 34. The FERM BP-6973 strain of *Lactobacillus clearans* was used, as was the FERM BP-7231 strain of *Enterococcus faecalis*. The aforementioned *Enterococcus faecalis* killed cell preparation was added in an amount of 1 g per L medium. The medium composition used for cultures comprised 10 g meat extract, 10 g peptone, 2 g glucose, 2 g NaCl, and 1 g $CaCO_3$ per liter, with the pH adjusted to 7.2, and was sterilized at high pressure for 15 minutes at 120° C. The tables below reveal that the inoculation of pathogens such as *E. coli* O-157, *Salmonella enteritidis*, and *Shigella flexneri* with *Lactobacillus clearans* and *Enterococcus faecalis* viable cells rapidly diminished the cell counts of such pathogens and resulted in their mutation to R types over the course of subculturing. *E. coli* O-157 mutated 100% to R type by the 13th subculture, and disappeared by the 15th subculture. *Salmonella enteritidis* and *Shigella flexneri* disappeared before mutating 100% to R type by the 13th and 15th subcultures, respectively. When *Lactobacillus clearans* was used by itself, as shown in Tables 11, 13, and 15, these pathogens mutated into R types over the course of numerous subcultures, but the bacteria maintained a constant cell count of 1 to $3 \times 10^9$ cells/mL, without disappearing. Although the addition of *Lactobacillus clearans* and *Enterococcus faecalis* killed cells to the aforementioned pathogens showed the same tendencies as that prevailing with the inoculation of viable cells, the mutation to R types was slower than that prevailing with the inoculation of viable cells, and the cell counts diminished but did not disappear. Nevertheless, the number of subcultures resulting in 100% mutation to R types was 15 with *E. coli* O-157, 30 with *Salmonella enteritidis*, and 15 with *Shigella flexneri*, which were far more rapid then when *Lactobacillus clearans* was used as inoculum on its own.

TABLE 29 effects of *Lactobacillus clearans* (FERM BP-6973) and *Enterococcus faecalis* (FERM BP-7231) viable cells on *E. coli* O-157

| Number Subculture | L. clearans FERM BP-6973 cells/mL | E. faecalis FERM BP-7231 cells/mL | E. coli O-157 S type cells/mL | E. coli O-157 R type cells/mL | Ratio of R type |
|---|---|---|---|---|---|
| 1 | $1 \times 10^9$ | $2 \times 10^9$ | $2 \times 10^9$ | 0 | 0 |
| 3 | $1 \times 10^9$ | $2.2 \times 10^9$ | $1.5 \times 10^9$ | 0 | 0 |
| 5 | $1.2 \times 10^9$ | $2.4 \times 10^9$ | $1 \times 10^9$ | $2 \times 10^8$ | 20% |
| 7 | $1 \times 10^9$ | $2 \times 10^9$ | $2 \times 10^8$ | $3 \times 10^8$ | 60% |
| 9 | $8 \times 10^8$ | $2.4 \times 10^9$ | $1 \times 10^8$ | $2 \times 10^8$ | 67% |
| 11 | $1 \times 10^9$ | $2.5 \times 10^9$ | 0 | $1 \times 10^8$ | 100% |
| 13 | $1.2 \times 10^9$ | $2.3 \times 10^9$ | 0 | $4 \times 10^7$ | 100% |
| 15 | $1.2 \times 10^9$ | $2.5 \times 10^9$ | 0 | 0 | |

TABLE 30 effects of *Lactobacillus clearans* (FERM BP-6973) and *Enterococcus faecalis* (FERM BP-7231) viable cells on *Salmonella enteritidis*

| Number Subculture | L. clearans FERM BP-6973 cells/mL | E. faecalis FERM BP-7231 cells/mL | E. coli O-157 S type cells/mL | E. coli O-157 R type cells/mL | Ratio of R type |
|---|---|---|---|---|---|
| 1 | $1 \times 10^9$ | $2.5 \times 10^9$ | $1.2 \times 10^9$ | 0 | |
| 3 | $1.2 \times 10^9$ | $2.5 \times 10^9$ | $1 \times 10^9$ | $2 \times 10^7$ | 2% |
| 5 | $1.5 \times 10^9$ | $2.2 \times 10^9$ | $8 \times 10^8$ | $5 \times 10^8$ | 38% |
| 7 | $1.3 \times 10^9$ | $3 \times 10^9$ | $1 \times 10^8$ | $1 \times 10^8$ | 50% |
| 9 | $1 \times 10^9$ | $3 \times 10^9$ | $7 \times 10^7$ | $8 \times 10^7$ | 53% |
| 11 | $1 \times 10^9$ | $3.2 \times 10^9$ | $3 \times 10^7$ | $5 \times 10^7$ | 63% |
| 13 | $8 \times 10^8$ | $3 \times 10^9$ | 0 | 0 | |
| 15 | $1 \times 10^9$ | $2.8 \times 10^9$ | 0 | 0 | |

TABLE 31 effects of *Lactobacillus clearans* (FERM BP-6973) and *Enterococcus faecalis* (FERM BP-7231) viable cells on *Shigella flexneri*

| Number Subculture | *L. clearans* FERM BP-6973 cells/mL | *E. faecalis* FERM BP-7231 cells/mL | *Shigella flexneri* S type cells/mL | R type cells/mL | Ratio of R type |
|---|---|---|---|---|---|
| 1 | $1.2 \times 10^9$ | $2 \times 10^9$ | $1.5 \times 10^9$ | 0 | 0 |
| 3 | $1 \times 10^9$ | $2.2 \times 10^9$ | $1 \times 10^9$ | 0 | 0 |
| 5 | $7 \times 10^8$ | $2.5 \times 10^9$ | $4 \times 10^8$ | $1 \times 10^8$ | 20% |
| 7 | $5 \times 10^8$ | $2.8 \times 10^9$ | $2 \times 10^8$ | $2 \times 10^8$ | 50% |
| 9 | $7 \times 10^8$ | $2.5 \times 10^9$ | $1 \times 10^8$ | $2 \times 10^8$ | 67% |
| 11 | $5 \times 10^8$ | $2.5 \times 10^9$ | $3 \times 10^7$ | $6 \times 10^7$ | 67% |
| 13 | $5 \times 10^8$ | $2.7 \times 10^9$ | $2 \times 10^6$ | $6 \times 10^6$ | 70% |
| 15 | $6 \times 10^8$ | $2.5 \times 10^9$ | 0 | 0 | |
| 17 | $8 \times 10^8$ | $3 \times 10^9$ | 0 | 0 | |

TABLE 32 effects of *Lactobacillus clearans* (FERM BP-6973) and *Enterococcus faecalis* (FERM BP-7231) killed cells on *E. coli* O-157

| Number subculture | *L. clearans* FERM BP-6973 cells/mL | *E. coli* O-157 S type cells/mL | R type cells/mL | Ratio of R type |
|---|---|---|---|---|
| 1 | $1.8 \times 10^9$ | $2.5 \times 10^9$ | 0 | 0 |
| 3 | $2 \times 10^9$ | $2 \times 10^9$ | 0 | 0 |
| 5 | $2 \times 10^9$ | $1.5 \times 10^9$ | $5 \times 10^8$ | 25% |
| 7 | $1.8 \times 10^9$ | $8 \times 10^9$ | $1 \times 10^9$ | 56% |
| 8 | $1.5 \times 10^9$ | $5 \times 10^8$ | $8 \times 10^8$ | 62% |
| 11 | $1.5 \times 10^9$ | $1 \times 10^8$ | $5 \times 10^8$ | 82% |
| 13 | $1.8 \times 10^9$ | $5 \times 10^7$ | $4.5 \times 10^8$ | 90% |
| 15 | $2 \times 10^9$ | 0 | $2 \times 10^8$ | 100% |
| 18 | $2 \times 10^9$ | 0 | $2 \times 10^8$ | 100% |

TABLE 33 effects of *Lactobacillus clearans* (FERM BP-6973) and *Enterococcus faecalis* (FERM BP-7231) killed cells on *Salmonella enteritidis*

| Number subculture | *L. clearans* FERM BP-6973 cells/mL | *Salmonella enteritidis* S type cells/mL | R type cells/mL | Ratio of R type |
|---|---|---|---|---|
| 1 | $1.5 \times 10^9$ | $3 \times 10^9$ | 0 | 0 |
| 3 | $1.2 \times 10^9$ | $2.5 \times 10^9$ | 0 | 0 |
| 5 | $1.2 \times 10^9$ | $1.5 \times 10^9$ | $7 \times 10^8$ | 32% |
| 7 | $1 \times 10^9$ | $1.2 \times 10^9$ | $1 \times 10^8$ | 45% |
| 9 | $1 \times 10^9$ | $8 \times 10^8$ | $1.2 \times 10^9$ | 60% |
| 11 | $8 \times 10^8$ | $5 \times 10^8$ | $8 \times 10^8$ | 61% |
| 13 | $8 \times 10^8$ | $5 \times 10^8$ | $5 \times 10^8$ | 50% |
| 15 | $5 \times 10^8$ | $2 \times 10^8$ | $8 \times 10^8$ | 80% |
| 20 | $7 \times 10^8$ | $1 \times 10^8$ | $9 \times 10^8$ | 90% |
| 25 | $5 \times 10^8$ | $2 \times 10^8$ | $1 \times 10^9$ | 83% |
| 30 | $4 \times 10^8$ | 0 | $1.8 \times 10^9$ | 100% |
| 35 | $5 \times 10^8$ | 0 | $1.5 \times 10^9$ | 100% |
| 40 | $6 \times 10^8$ | 0 | $1 \times 10^9$ | 100% |

TABLE 34 effects of *Lactobacillus clearans* (FERM BP-6973) and *Enterococcus faecalis* (FERM BP-7231) killed cells on *Shigella flexneri*

| Number subculture | *L. clearans* FERM BP-6973 cells/mL | *Shigella flexneri* S type cells/mL | R type cells/mL | Ratio of R type |
|---|---|---|---|---|
| 1 | $1.2 \times 10^9$ | $3.5 \times 10^9$ | 0 | 0 |
| 3 | $1 \times 10^9$ | $3 \times 10^9$ | 0 | 0 |
| 5 | $7 \times 10^8$ | $2.5 \times 10^9$ | $2 \times 10^8$ | 7.4% |
| 7 | $6 \times 10^8$ | $2 \times 10^9$ | $3 \times 10^8$ | 13% |
| 9 | $7 \times 10^8$ | $2 \times 10^9$ | $1 \times 10^9$ | 33% |
| 11 | $5 \times 10^8$ | $2 \times 10^9$ | $1 \times 10^9$ | 33% |
| 13 | $5 \times 10^8$ | $1.8 \times 10^9$ | $1.2 \times 10^9$ | 40% |
| 15 | $4 \times 10^8$ | $1.8 \times 10^9$ | $1.5 \times 10^9$ | 45% |
| 20 | $5 \times 10^8$ | $1.5 \times 10^9$ | $1.8 \times 10^9$ | 55% |
| 25 | $6 \times 10^8$ | $1 \times 10^9$ | $1.5 \times 10^9$ | 60% |
| 30 | $4.5 \times 10^8$ | $8 \times 10^8$ | $1.8 \times 10^9$ | 69% |
| 35 | $4 \times 10^8$ | $3 \times 10^8$ | $2 \times 10^9$ | 87% |
| 40 | $3.5 \times 10^8$ | $1 \times 10^8$ | $2 \times 10^9$ | 95% |
| 45 | $4 \times 10^8$ | 0 | $2 \times 10^9$ | 100% |
| 50 | $4 \times 10^8$ | 0 | $2 \times 10^9$ | 100% |

Example 6

A viable cell preparation of *Lactobacillus clearans* FERM BP-6972 or *Lactobacillus clearans* FERM BP-6972 prepared by the method in Manufacturing Example 1, a viable cell preparation of *Enterococcus faecalis* FERM BP-7230 or *Enteroccus faecalis* 7231 prepared by the method in Manufacturing Example 2, and a killed cell preparation of *Enterococcus faecalis* FERM BP-7230 or *Enterococcus faecalis* 7231 prepared by the method in Manufacturing Example 3 were combined and added to feed, which was given to groups of five 10-week old male mice. 1 g feed contained $5 \times 10^8$ cells *Lactobacillus clearans* and $5 \times 10^8$ cells *Enterococcus faecalis* ($2.5 \times 10^8$ cells each of viable and killed cells when used in combination). The animals were allowed to feed freely for 3 months. The triglycerides and cholesterol in serum were measured for comparison with levels in control mice fed only normal feed. The triglycerides were measured with a Triglyceride E-Test Wako, while the cholesterol was measured with a Triglyceride C-Test Wako. The mean levels for each group were obtained. The mean level for the mice in the control group was 100%. The results are given in Table 35. Tables 35 and 21 show that the addition of viable or killed, as well as viable and killed, cells of *Enterococcus*

*faecalis*, which have action in lowering triglycerides and cholesterol, to *Lactobacillus clearans* was far more effective than when *Enterococcus faecalis* was administered alone. Unlike the results obtained when administered alone, the combined use of killed cells resulted in greater effects than viable cells. Compared to the control group, levels decreased as much as about ½.

TABLE 35 effect of mixture of *Lactobacillus clearans* and *Enterococcus faecalis* on triglycerides and cholesterol in mouse serum

| Lactobacillus clearans FERM BP-No. | Enterococcus faecalis FERM BP-No. | | Triglycerides | Cholesterol |
|---|---|---|---|---|
| | Viable cells | Killed cells | | |
| 6972 | 7230 | | 60% | 55% |
| 6972 | | 7230 | 55% | 47% |
| 6972 | 7230 | 7230 | 58% | 52% |
| 6971 | 7231 | | 57% | 55% |
| 6971 | | 7231 | 50% | 45% |
| 6971 | 7231 | 7231 | 52% | 50% |

Example 7

7 groups comprising a total of thirty five 8-week old spontaneous hypertensive rats (SHR) were raised for 7 months on feed containing the cell preparations of Example 6. The blood pressure was measured before and after administration to groups given each type of cell preparation and the control group, with the results given in Table 36. Tables 36 and 22 reveal that the blood pressure had improved, on average, about 15% after 3 months. The killed cells of *Enterococcus faecalis* had more effective action than the viable cells, in the same manner as in Example 6. The drop in blood pressure was about 10 to 20%, results which were better than those obtained when *Enterococcus faecalis* was administered by itself.

TABLE 36 effect of mixture of *Lactobacillus clearans* and *Enterococcus faecalis* on rat blood pressure

| Lactobacillus clearans FERM BP-No. | Enterococcus faecalis FERM BP-No. | | Mean level before admin. (mmHg) | Mean level after admin. (mmHg) | Decrease |
|---|---|---|---|---|---|
| | Viable cells | Killed cells | | | |
| 6971 | 7230 | | 210 | 180 | 14.3% |
| 6971 | | 7230 | 203 | 168 | 17.2% |
| 6971 | 7230 | 7230 | 200 | 175 | 12.5% |
| 6973 | 7231 | | 207 | 176 | 15.0% |
| 6973 | | 7231 | 198 | 162 | 18.2% |
| 6973 | 7231 | 7231 | 205 | 178 | 13.1% |
| Control | | | 202 | 210 | 3.9% increase |

Table 37 shows the action in terms of various functions with the use of *Lactobacillus clearans*, *Enterococcus faecalis*, and both.

TABLE 37

Comparative summary

| Parameter | Lactobacillus clearans | Enterococcus faecalis | L. clearans and E. faecalis |
|---|---|---|---|
| Decrease of toxic, malodorous intestinal putrefying substances | ○ to □ | Δ | ⊚ |
| Feces deodorization | □ | Δ | ⊚ |
| Growth of beneficial enteric bacteria | ○ to □ | Δ | ⊚ |
| Suppression of harmful enteric bacteria | ○ | Δ | ⊚ |
| Antiflatulent action | ○ | Δ | ⊚ |
| Suppression of pathogen growth | Δ | Δ | ⊚ |
| Suppression of pathogen toxicity | ○ | x | ⊚ |
| Triglyceride reduction | Δ | ○ to □ | ⊚ |
| Cholesterol reduction | Δ | ○ to □ | ⊚ |
| Hypotensive action | Δ | □ | ○ to ⊚ |
| Overall evaluation | Perceptible results with preserving health, stimulating recovery, preventing aging | Imperceptible, but results gradually appear with moderate to prolonged use | Rapid, perceptible, highly effective results |

*: excellent; ○: good; □: ordinary; Δ: weak; x: none

Health care and related approaches have gradually changed in our increasingly aging society. Our time, where the treatment of acute diseases and chronic diseases has been regarded with the utmost importance, is witnessing a shift, now or in the near future, to "preventive medicine", and even "nutritional therapy," in light of our older society. These are not treatments which are undertaken after illness sets in. Rather, approaches for creating health on one's own through a more educated intake of nutrition are now increasingly in the mainstream in order to naturally prevent illness. It is not overstating the case to suggest that the prevention of disease to avoid the need for treatment at all is in the vanguard of treatment in the 21st century.

The oral administration of the lactic acid bacteria preparation of the present invention gradually extends the influence of beneficial intestinal bacteria, steadfastly guards the intestinal mucosa, produces vitamins, and synthesizes amino acids, all the while suppressing the growth of foreign bacteria and foreign pathogens, diminishing their toxicity, and activating immunological functions under the guidance of the lactic acid bacteria of the preparation. Harmful intestinal bacteria are thus markedly reduced, and the production of malodorous putrefying substances is suppressed, resulting in significantly deodorized feces. As if under attack, the lactic acid bacteria of the preparation actively feeds on the intestinal putrefying substances, resulting in a cleaner intestinal environment and the normalization of the intestinal mucosa and surrounding vessels and nerves.

Purification of the intestines, which are the wellspring of human vitality, energy, blood and flesh, results in better absorption of vital substances and conversely in fewer toxic substances absorbed through the intestines. This inevitably results in better hepatic function, and thus in lower triglycerides and cholesterol in serum, as well as cleaner blood. Such revitalized blood results in lower blood pressure, so that vital substances such as hormones, enzymes, antibodies, and immunological substances are not prevented from being distributed throughout the body's entire system. Metabolism is thus improved, and all systemic functions are invigorated. That is, the polluted intestines are cleaned and allowed to return to their pristine condition, resulting in an overall improvement and a vital state of health with no hint of illness. It can be said that Metchnikoff's doctrine on longevity is now being realized a century later.

The lactic acid bacteria preparation of the present invention can be stored without any loss of titer for 2 to 3 years, allowing it to be produced in the form of portable goods which can be readily used anywhere at any time, and is thus of immeasurable value. In societies with populations of increasingly advanced age, more and more elderly individuals are likely to become bedridden; although the disposal of waste can become a problem, the deodorization of such waste would make such a task that much less disagreeable, and could be of service to caretakers.

What is claimed is:

1. A lactic acid bacteria preparation, comprising viable cells of *Lactobacillus clearans*, and killed cells of *Enterococcus faecalis*, wherein the preparation reduces one or more of at least triglycerides and cholesterol.

2. A lactic acid bacteria preparation, comprising viable cells of *Lactobacillus clearans*, and viable and killed cells of *Enterococcus faecalis*, wherein the preparation reduces one or more of at least triglycerides and cholesterol.

* * * * *